United States Patent
Kampen

[11] Patent Number: 6,156,563
[45] Date of Patent: Dec. 5, 2000

[54] METHOD FOR CLARIFYING CANE SUGAR JUICE

[75] Inventor: Willem H. Kampen, Baton Rouge, La.

[73] Assignee: Board of Supervisors of Louisiana State University and Agricultural and Mechanical College, Baton Rouge, La.

[21] Appl. No.: 09/237,017

[22] Filed: Jan. 25, 1999

Related U.S. Application Data

[60] Provisional application No. 60/228,807, Jan. 29, 1998.

[51] Int. Cl.[7] ............................... C12S 3/10; A23L 1/015
[52] U.S. Cl. ............................ 435/276; 426/52; 210/632
[58] Field of Search .................................. 435/274, 275, 435/276; 210/632; 426/52, 54

[56] References Cited

U.S. PATENT DOCUMENTS

| | | | |
|---|---|---|---|
| 2,615,053 | 10/1952 | Artz et al. | |
| 3,767,526 | 10/1973 | Suzuki et al. | 195/11 |
| 3,808,050 | 4/1974 | Paley | 127/55 |
| 4,332,622 | 6/1982 | Hohnerlein, Jr. et al. | 127/41 |
| 4,914,029 | 4/1990 | Caransa et al. | 435/101 |
| 5,262,328 | 11/1993 | Clarke et al. | 436/17 |
| 5,436,156 | 7/1995 | Van Gorcom et al. | 435/252.3 |
| 5,443,979 | 8/1995 | Vanderbeke et al. | |
| 5,482,631 | 1/1996 | Saska et al. | 210/635 |
| 5,554,399 | 9/1996 | Vanderbeke et al. | 426/49 |

FOREIGN PATENT DOCUMENTS 0 321 004    6/1989    European Pat. Off.

*Primary Examiner*—William H. Beisner
*Attorney, Agent, or Firm*—John H. Runnels

[57] ABSTRACT

A new method for clarifying sugar cane juice is disclosed. Treating the phytic acid (or phytate) in sugar cane juice with phytase and acid phosphatase converts the phytic acid to inositol and inorganic phosphate, thereby improving the clarification of the sugar juice substantially. The valuable product inositol results as a consequence of the hydrolysis of phytic acid. The process is environmentally friendly, as it requires only the addition of small amounts of enzymes to existing sugar clarification processes. It does not cause inversion of sucrose to other sugars, and does not cause color formation. The extra phosphate released by this process is available to react with milk of lime, thus improving subsequent flocculation and consequent clarification.

3 Claims, No Drawings

METHOD FOR CLARIFYING CANE SUGAR JUICE

The benefit of the Jan. 29, 1998 filing date of provisional application No. 60/228,807 (which was a conversion of nonprovisional application 09/015,799) is claimed under 35 U.S.C. § 119(e).

This invention pertains to a method of clarifying cane sugar juice.

A critical step in the manufacture of either raw sugar or white sugar is clarification of the sugar juice. Several clarification methods are currently used, including cold liming, hot liming, fractional liming, fractional liming with double heating, and calcium saccharate (sucrate) treatment. The limed juice is typically heated above its boiling point under pressure, and flashed to atmospheric pressure to remove non-condensable gases that would inhibit settling of impurities, and an anionic flocculent is added to improve settling of flocs in the clarifier. Flocculation removes insoluble suspended particles and colloidal impurities by aggregating them into flocs. A typical size range for pre-flocculation impurities in mill-extracted, mixed juices at Louisiana raw sugar factories is 0.1–22 microns.

Fluctuations in the rate of settling, the turbidity of the juice, or the filterability of the precipitate can result from different cane varieties, soils, fertilizer applications, climatic conditions, and other conditions. To obtain high quality clarified juices, removal of components other than sucrose should be maximized, and losses of sucrose and formation of color should be minimized. Proteinaceous and waxy matter, some silicic acid (hydrated $SiO_2$), and sesquioxides can be removed by heating, while liming neutralizes acids, forms calcium phosphates, and coagulates colloidal particles. The colloids are primarily anionic and hydrophilic. The colloids are usually surrounded by a water layer, which must be destroyed to allow removal of the colloids by settling. Hydrophobic colloids (waxes, pectins, proteins) are less hydrated, and have a relatively smaller effect on viscosity.

The presence of colloids in sugar juice tends to increase the hydration of the particles present, making them gelatinous and slow to settle. Colloids must be removed, as they increase the viscosities of syrups and molasses, decrease filtration rates, decrease rates of sucrose crystallization, and tend to increase color. Colloidal particles in sugar juice usually carry a negative charge, which causes them to repel one another, thus inhibiting their coalescence. Divalent and trivalent cations, which bind more tightly to colloidal micelles than do monovalent cations, tend to reduce the zeta potential of the colloids, improving the tendency of the particles to form aggregates and to flocculate. In particular, calcium is frequently used to foster flocculation.

High levels of inorganic phosphate in sugar juice promote the removal of silicic acid and waxy-lime material. Sugar cane juice contains both organic and inorganic forms of phosphorus, the latter comprising primarily free phosphate ions. In prior juice clarification techniques, only free inorganic phosphate ions have played a substantial part in reactions with calcium. Generally, good quality clarified juice can be obtained when about 300 mg/l of inorganic phosphate (measured as $P_2O_5$) is present. Much higher levels of phosphate (500–800 ppm) not only cause large mud volumes, but they also tend to form light flocs that settle slowly.

High sucrose extraction efficiencies (e.g., 95% in mill tandems and 99% in diffusers) cause increased extraction of non-sugars. Cane juices contain a considerable amount of silicic acid, typically 10 to 30% of total mineral ash content, depending on the cane quality and the extraction techniques used. Silicic acid usually forms negatively-charged colloids. Sesquioxides are present in much smaller quantities than silicic acid. Ferric oxide levels typically increase somewhat during clarification due to loss of metal from mill machinery into the juice. The ratio of inorganic phosphate to silicic acid (plus sesquioxides) is the main parameter used to predict the behavior of cane juice during clarification, especially its settling characteristics and mud volume percentage. This so-called "Bogstra ratio," $P_2O_5/(SiO_2+Fe_2O_3+Al_2O_3)$ (measured by mass densities) should be at least about 0.20–0.25 (depending on aconitic acid levels in the juice) to produce a clear clarified juice with low suspended solid levels. Thus (within limits), higher levels of inorganic phosphate are beneficial to clarification.

The Bogstra ratio may be 0.20 or even slightly lower and still yield a clarified juice of reasonable quality, if the cane juice is high in aconitic acid. High aconitic acid levels typify juice from areas where cane is harvested while still slightly immature, such as Louisiana. Aconitic acid and the amino acids present are the principal factors in determining the natural pH of cane juice. A given quantity of lime will bind 1.776 times more of the first hydrogen of aconitic acid than the first hydrogen of phosphoric acid, but 565 times more of the second hydrogen of aconitic acid than the second hydrogen atom of phosphoric acid. The percentage of juice phosphate eliminated in clarification is inversely related to the concentration of aconitic acid in the juice. Hence, high levels of aconitic acid increase the buffering capacity of the juice, and cause high mud volumes. Calcium aconitate is only removed to a large extent if the pH of the limed juice is at least 8.0–8.5. Phosphoric acid has been added to juice to overcome this problem, to increase phosphate levels and to improve clarification. A drawback of this approach is the relatively high cost of phosphoric acid.

Phytic acid (1,2,3,4,5,6-cyclohexanehexolphosphoric acid) is present in sugar cane juice, but has previously been little studied, if in fact it has been studied at all. The inventor is aware of no previous publications mentioning that phytic acid is even a component of sugar cane juice.

The enzyme phytase, produced by Gist-brocades and marketed by BASF under the name Natuphos™, has been used in animal nutrition in Europe since 1991 and in the USA since 1996. The enzyme has been prepared commercially by fermentation of a genetically modified *Aspergillus niger* strain. Phytase releases phosphorus from phytic acid or phytate, yielding inorganic phosphate, inositol-monophosphate, and di- and tri-valent phytate bound to cations or proteins. Phytase does not cleave all phosphate from phytic acid, and typically breaks off the phosphate groups from the respective carbon atoms in the following order: 3, 4, 5, 6, and 1. The phosphate group at position 2 may not be removed, leaving inositol monophosphate, which is freely soluble in water. The final phosphate group may be released by an acid phosphatase, yielding inositol, a valuable product with a present list price of approximately $22.00/kg.

U.S. Pat. No. 5,436,156 discloses a cloned phytase gene.

U.S. Pat. No. 4,914,029 discloses that phytic acid is a component of corn or sorghum steep liquor, and that phytic acid may be converted to inositol by treatment with phytase and acid phosphatase.

U.S. Pat. No. 5,554,399 discloses the treatment of certain plant raw materials with phytase and acid phosphatase to hydrolyze phytic acid to inorganic phosphate and inositol.

A new method has been discovered to improve the clarification of sugar cane juice. A previously unrecognized and untapped source of phosphate has been identified that is naturally present in sugar cane juice. A method to free that phosphate for clarification has been discovered. Thus clarification may be accomplished more economically, and in an environmentally friendly manner. A valuable by-product also results from the novel treatment.

In particular, sugar cane juice naturally contains phytic acid. Treating the phytic acid (or phytate) with phytase and acid phosphatase converts the phytic acid to inositol and inorganic phosphate, thereby improving the clarification of the sugar juice substantially. The valuable product inositol results as a consequence of the hydrolysis of phytic acid. The process is environmentally friendly, as it requires only the addition of small amounts of enzymes to existing sugar clarification processes. It does not cause inversion of sucrose to other sugars, and does not cause color formation. The extra phosphate released by this process is available to react with milk of lime ($Ca(OH)_2$), thus improving subsequent flocculation and consequent clarification.

The use of acid phosphatase to remove the final phosphate group from phytic acid is an optional, but preferred step in the new clarification method. The acid phosphatase increases total levels of inorganic phosphate, and results in the production of free inositol. Without the acid phosphatase, free phosphate would still be produced (although in smaller concentrations), and the less valuable inositol monophosphate would be produced instead of inositol.

Commercially-obtained Natuphos™ 5000 L was tested in Louisiana sugar cane mixed juice. Natuphos™5000 L is a brown liquid with a density of 1.2 g/ml, and a minimum activity of 5000 FTU per gram. One phytase unit (FTU) is defined as the quantity of enzyme that will liberate 1 micromole of inorganic phosphorous per minute from an excess of sodium phytate at pH 5.5 and 37° C. Factors affecting phytase activity include pH, temperature, moisture, and exposure time. Optimum conditions to form inorganic phosphate from mixed cane juice with Natuphos™ 5000L were found to be 25–35° C., pH 5.2–5.4. Activity was close to 100% over the pH range 4.6–6.2. The activity was reduced to approximately 30% at pH 7.0. Sufficient residence time for phytase before liming is important; this time varies depending on the concentration in a particular case. The enzyme loses essentially all activity at a temperature of approximately 77° C. Thus heating the juice above this temperature prior to entering the clarifier will inactivate the enzyme. Sufficient overall reaction time should be allowed for the enzyme to perform its task at low cost.

Prototype factory tests were carried out at three enzyme dosage levels: 19, 29, and 36 ppm (v/v). The enzyme was added to the primary juice following the first milling, which included the crusher juice. The juice was thereafter processed in accordance with typical clarification procedures. The cane processed during these tests was a combination of cut-chopped and whole stalks, washed on a wash table to remove field mud. The cane was prepared for extraction by two sets of revolving knives and a crusher. Extraction was conducted in a five-mill tandem with a standard imbibition system. Juice from the crusher and the first mill (undiluted cane juice) was combined to form the primary juice. Phytase was added to the juice immediately following the first mill, to maximize the reaction time. Juice from the second mill (remaining cane juice diluted with imbibition water) and the primary juice were combined in a buffer tank to form mixed juice. At prevailing operating conditions, the primary juice required between 1 and 1½ minutes to enter the mixed juice tank. Residence time in the mixed juice tank was 4 to 5 minutes. Following suction from the mixed juice tank, milk of lime (calcium hydroxide) was added to raise the juice pH from approximately 5.4 to about 7.1 to 7.2. Thus the enzyme had about 5 to 6½ minutes reaction time at an activity level of essentially 100%. The increase in pH decreased the activity to around 25%. The limed juice was then pumped to one of four volumetric holding tanks and then to the juice heaters, where the temperature increased to 105° C., inactivating the enzyme. Available reaction time at pH 7.1 to 7.2 was about 14 to 16 minutes. Next, the juice was allowed to flash by reducing the pressure from approximately 35 psig to atmospheric. The anionic flocculent Talosep 3A (Tate & Lyle) was added to speed the settling of mud and other particulate and colloidal matter in the clarifier. Clarifier residence time was around 80 to 90 minutes. The clear supernatant (clarified juice) was then pumped to the evaporator station to be concentrated before sugar boiling began.

Phosphate levels in mixed juice and in clarified juice were determined by HPLC, both with and without addition of enzyme. See Table I.

TABLE 1

Effect of Phytase Concentration, Time, and pH on Inorganic Phosphate Formation at 21° C.

| Sample Number | pH | Total Reaction Time (mins) | Phyrase, as % Natuphos ™ (v/v) | phosphate concentration, ppm, as $P_2O_5$ (w/v) |
|---|---|---|---|---|
| 1 | 5.4 | 0 | 0.00 | 180.9 |
| 2 | 5.4 | 10 | 0.05 | 220.8 |
| 3 | 5.4 | 20 | 0.05 | 256.9 |
| 4 | 5.4 | 30 | 0.05 | 282.6 |
| 5 | 5.7 | 10 | 0.10 | 239.5 |
| 6 | 5.7 | 20 | 0.10 | 278.5 |
| 7 | 5.7 | 30 | 0.10 | 301.4 |
| 8 | 6.9 | 10 | 0.10 | 187.3 |
| 9 | 6.9 | 20 | 0.10 | 203.8 |
| 10 | 6.9 | 30 | 0.10 | 217.1 |

The higher the phosphate level in the juice, the better the clarified juice quality will be (as measured by turbidity). The lower the turbidity, the lower the suspended solids concentration (although the relationship is not linear). For comparison, the inventor is aware of a factory where (via a different technique), a reduction in suspended solids in the clarified juice of only 10 ppm resulted in the removal of approximately 75 pounds per hour of non-sugars and other impurities; these impurities then did not end up in the evaporators as scale, nor in the raw sugar or molasses to cause sugar losses.

The total reaction time available for the enzyme through the mill tandem juice collection trough, the mixed juice tanks, the liming station, the volumetric measurements station, and the juice heaters is typically about 20 minutes. At 36 ppm total added Natuphos, inorganic phosphate levels increased from 407 to 563 ppm (measured as $P_2O_5$), while the turbidity was reduced from 9.4 to 6.0 NTU/brix. In all cases, the addition of phytase resulted in a better clarified juice.

Acid phosphatase was obtained from Shin Nihon Chemical under the name Sumizyme PM-L™. The enzyme is produced commercially from *Aspergillus niger*. The activity was 3,000 units per gram at pH 4.5 and 37° C., measured by its effect on the decomposition of p-nitrophenylphosphate. The enzyme was reported by the manufacturer to be stable over the pH range 5–7, with optimum relative activity at pH 5.0. At pH 6.5 the relative activity is reduced to 10% of maximum activity. Heating the enzyme to 85° C. for 15 minutes destroys all activity. (Optimum pH depends on the reaction mixture and conditions used. As shown in Table 2, we observed the optimum pH for our reaction conditions to be approximately 5.6.)

Results of a ten-minute reaction of acid phosphatase with inositol monophosphate produced by phytase are given in Table 2. For the experiments shown in Table 2, the feedstock used was mixed juice from a Louisiana sugar factory, stored on ice until used. Reaction was carried out at 21° C. Initially, phytase was added to the juice, and the juice was allowed to stand until the conversion of phytic acid to inositol monophosphate and inorganic phosphate was essentially complete. Then acid phosphatase was added, and inositol levels after ten minutes were measured. In all cases the starting concentration of inositol was 188.1 ppm (i.e., the amount of inositol naturally present in the juice). Depending on reaction conditions, the level of inositol after reaction more than doubled following acid phosphatase treatment.

TABLE 2

Effect of Acid Phosphatase Concentration and pH on Inositol Formation from Inositol Monophosphate.

| Sample Number | pH | Acid Phosphatase Concentration, Units/ml | Inositol Concentration following reaction with Acid Phosphatase | Net Inositol Produced, ppm (w/v) |
| --- | --- | --- | --- | --- |
| 11 | 5.4 | 6.32 | 197.0 | 8.9 |
| 12 | 5.4 | 12.64 | 255.9 | 67.8 |
| 13 | 5.6 | 6.32 | 340.2 | 152.1 |
| 14 | 5.6 | 12.64 | 392.8 | 204.7 |
| 15 | 6.0 | 6.32 | 243.0 | 54.9 |
| 16 | 6.0 | 12.64 | 290.3 | 102.2 |

Both enzymes should be added during the earliest practical process step to maximize available reaction time. To simplify procedures, the enzymes may simply be sprayed onto the cane just before the cane is fed to the crusher. An alternative would be to use a buffer tank to impart a residence time on the mixture of juice and enzymes.

Although the principal effect of the novel process is to liberate inorganic phosphate from phytic acid, it is likely that smaller amounts of inorganic phosphate will incidently be released from other organic phosphate sources in sugar juice as well, for example nucleic acids such as adenosine triphosphate. The presence and concentration of other phytase-sensitive organic phosphate sources will depend on many factors, including plant variety, growth conditions, maturity at harvest, etc.

Techniques known in the art may be used to recover the produced inositol as a valuable by-product, e.g., the technique disclosed in U.S. Pat. No. 5,482,631.

The complete disclosures of all references cited in this specification are hereby incorporated by reference. In the event of an otherwise irreconcilable conflict, however, the present specification shall control.

I claim:

1. A process for claiming a sugar cane juice that contains suspended particulate matter, comprising the steps of:

(a) reacting the juice with phytase under reaction conditions sufficient to cause a significant amount of the phytic acid or phytate that is inherently present in the sugar cane juice to be converted to inositol monophosphate and inorganic phosphate, whereby the concentration of inorganic phosphate in the juice is substantially increased; and (b) subsequently reacting the juice with calcium hydroxide and a flocculent under reaction conditions sufficient to cause substantially all of the suspended particular matter to settle from the juice; whereby a clarified juice is produced.

2. A process as recited in claim 1, additionally comprising the step of reacting the juice with acid phosphatase under reaction conditions sufficient to cause a significant amount of the inositol monophosphate to be converted to inositol and inorganic phosphate, whereby the concentration of inorganic phosphate in the juice is substantially increased.

3. A process as recited in claim 2, additionally comprising the step of recovering inositol from the juice.

* * * * *